US00PP20031P2

(12) United States Plant Patent
Barends

(10) Patent No.: US PP20,031 P2
(45) Date of Patent: May 26, 2009

(54) ***GERANIUM* PLANT NAMED 'FISUM DARK RED'**

(50) Latin Name: *Pelargonium ×hortorum*
Varietal Denomination: Fisum Dark Red

(75) Inventor: Eveline Barends, De Lier (NL)

(73) Assignee: Fides B.V., De Lier (NL)

( * ) Notice: Subject to any disclaimer, the term of this patent is extended or adjusted under 35 U.S.C. 154(b) by 0 days.

(21) Appl. No.: 12/154,249

(22) Filed: May 21, 2008

(51) Int. Cl.
*A01H 5/00* (2006.01)

(52) U.S. Cl. ..... Plt./330
(58) Field of Classification Search ..... Plt./330
See application file for complete search history.

*Primary Examiner*—Kent L Bell
(74) *Attorney, Agent, or Firm*—C. A. Whealy

(57) ABSTRACT

A new and distinct cultivar of Zonal *Geranium* plant named 'Fisum Dark Red', characterized by its upright and slightly outwardly spreading growth habit; rounded plant habit; freely basal branching habit; dark green-colored leaves; freely flowering habit; semi-double dark red-colored flowers; and good garden performance.

1 Drawing Sheet

Botanical designation: *Pelargonium×hortorum*.
Cultivar denomination: 'Fisum Dark Red'.

BACKGROUND OF THE INVENTION

The present invention relates to a new and distinct cultivar of Zonal *Geranium*, botanically known as *Pelargonium× hortorum,* and hereinafter referred to by the name 'Fisum Dark Red'.

The new Zonal *Geranium* is a product of a planned breeding program conducted by the Inventor in De Lier, The Netherlands. The objective of the breeding program is to create new compact, freely-branching and freely-flowering Zonal *Geranium* cultivars that flower early and have attractive foliage and flower coloration.

The new Zonal *Geranium* originated from a cross-pollination made by the Inventor in De Lier, The Netherlands of two unnamed proprietary selections of *Pelargonium×hortorum,* not patented, in August, 2004. The cultivar Fisum Dark Red was discovered and selected by the Inventor as a flowering plant from within the progeny of the stated cross-pollination in a controlled greenhouse environment in De Lier, The Netherlands, in 2004.

Asexual reproduction of the new Zonal *Geranium* by vegetative terminal cuttings in a controlled greenhouse environment in De Lier, The Netherlands, since 2004, has shown that the unique features of this new Zonal *Geranium* are stable and reproduced true to type in successive generations.

SUMMARY OF THE INVENTION

The cultivar Fisum Dark Red has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Fisum Dark Red'. These characteristics in combination distinguish 'Fisum Dark Red' as a new and distinct cultivar of Zonal *Geranium*:

1. Upright and slightly outwardly spreading growth habit; rounded plant habit.
2. Freely basal branching habit.
3. Dark green-colored leaves.
4. Freely flowering habit.
5. Semi-double dark red-colored flowers.
6. Good garden performance.

Plants of the new Zonal *Geranium* differ primarily from plants of the parent selections in plant size and uniformity as plants of the new *Geranium* are more compact and more uniform than plants of the parent selections.

Plants of the new Zonal *Geranium* can be compared to plants of *Pelargonium×hortorum* 'Fisum Red', disclosed in U.S. Plant Pat. No. 16,106. In side-by-side comparisons conducted in De Lier, The Netherlands, plants of the new Zonal *Geranium* differed from plants of 'Fisum Red' primarily in flower color as plants of the new Zonal *Geranium* have darker red-colored flowers than plants of 'Fisum Red'.

BRIEF DESCRIPTION OF THE PHOTOGRAPH

The accompanying colored photograph illustrates the overall appearance of the new Zonal *Geranium*, showing the colors as true as it is reasonably possible to obtain in colored reproductions of this type. Colors in the photograph may differ slightly from the color values cited in the detailed botanical description which accurately describe the colors of the new Zonal *Geranium*. The photograph comprises a side perspective view of a typical flowering plant of 'Fisum Dark Red' grown in a container.

DETAILED BOTANICAL DESCRIPTION

The aforementioned photograph and following observations, measurements and values describe plants grown in De Lier, The Netherlands in a glass-covered greenhouse during the autumn and winter and under conditions which closely approximate commercial production. During the production of the plants, day temperatures ranged from 12° C. to 20° C. and night temperatures ranged from 9° C. to 16° C. Plants were twelve weeks old when the photograph and the description were taken. In the detailed description, color references are made to The Royal Horticultural Society Colour Chart, 1995 Edition, except where general terms of ordinary dictionary significance are used.

Botanical classification: *Pelargonium×hortorum* 'Fisum Dark Red'.

Parentage:

*Female, or seed, parent.*—Unnamed proprietary selection of *Pelargonium×hortorum,* not patented.

*Male or pollen parent.*—Unnamed proprietary selection of *Pelargonium×hortorum,* not patented.

Propagation:

*Type.*—By vegetative terminal cuttings.

*Time to initiate roots, summer.*—About four days at temperatures of 22° C.

*Time to initiate roots, winter.*—About seven days at temperatures of 22° C.

*Time to produce a rooted young plant, summer.*—About 16 days at temperatures of 22° C. to 30° C.

*Time to produce a rooted young plant, winter.*—About 21 days at temperatures of 20° C. to 25° C.

*Root description.*—Medium in thickness, fibrous; whitish grey in color.

*Rooting habit.*—Freely branching, moderately dense.

Plant description:

*General appearance.*—Upright and outwardly spreading growth habit; rounded and uniformly mounded plant habit; densely foliated.

*Growth and branching habit.*—Moderately vigorous to vigorous growth habit. Freely basal branching habit with about four or five basal branches developing per plant.

*Plant height, to top of umbels.*—About 30 cm to 32 cm.

*Plant width.*—About 28 cm.

*Lateral branches.*—Length: About 6 cm to 8 cm. Diameter: About 5 mm to 8 mm. Internode length: About 1 cm to 3 cm. Texture: Pubescent. Strength: Strong, sturdy. Color: Close to 144B.

Foliage description:

*Arrangement.*—Alternate; simple.

*Length* (*including petiole*).—About 11 cm to 13 cm.

*Width.*—About 7 cm to 9 cm.

*Shape.*—Orbicular.

*Apex.*—Rounded.

*Base.*—Cordate.

*Margin.*—Crenate; slightly undulate.

*Venation pattern.*—Palmate.

*Texture, upper and lower surfaces.*—Densely pubescent.

*Color.*—Developing foliage, upper surface: Close to 137C. Developing foliage, lower surface: Close to 146B. Fully developed, upper surface: Close to 137B; venation, close to 144C. Fully developed, lower surface: Close to 146A; venation, close to 144C. Zonation pattern: Faint, close to 177A in color.

*Petiole.*—Length: About 3 cm to 7 cm. Diameter: About 2 mm to 3 mm. Texture, upper and lower surfaces: Pubescent. Color, upper and lower surfaces: Close to 144A.

Flower description:

*Flower arrangement.*—Semi-double rotate flowers arranged in rounded hemispherical umbels arising from apical leaf axils. Umbels displayed above the foliage on strong peduncles. Flowers face upright to outward. Flowers not fragrant.

*Quantity of flowers.*—Freely flowering habit; about nine to eleven umbels develop per plant, each umbel with about 12 to 30 flowers.

*Flowering season.*—Year-round under greenhouse conditions. In an outdoor nursery in De Lier, The Netherlands, flowering is continuous from late spring until frost in the autumn.

*Flower longevity.*—Individual flowers last about two to eight days on the plant. Flowers persistent.

*Umbel height.*—About 5 cm to 8 cm.

*Umbel diameter.*—About 5 cm to 8 cm.

*Flower diameter.*—About 4 cm to 5 cm.

*Flower depth* (*height*).—About 4 cm to 5 cm.

*Flower buds.*—Length: About 2 mm to 19 mm. Diameter: About 2 mm to 15 mm. Shape: Globular to elliptical. Color: Close to 144B.

*Petals.*—Quantity per flower: About five to 14. Length: About 2.5 cm to 2.8 cm. Width: About 2.5 cm to 2.8 cm. Shape: Spatulate to obovate. Apex: Rounded. Base: Attenuate. Margin: Entire. Texture, upper and lower surfaces: Smooth, glabrous. Color: When opening and fully opened, upper surface: Between 45A and 53B; color becoming closer to 53C with development. When opening and fully opened, lower surface: Close to 46C.

*Petaloids.*—Quantity per flower: Typically one. Length: About 1 mm to 2 cm. Width: About 2 mm to 2 cm. Shape: Irregularly shaped; obovate to irregularly oblanceolate. Apex: Rounded. Base: Attenuate. Margin: Entire. Texture, upper and lower surfaces: Smooth, glabrous. Color: When opening, upper and lower surfaces: Between 45A and 53C. Fully opened, upper and lower surfaces: Between 45A and 53C.

*Sepals.*—Quantity per flower: Five, arranged in a single whorl. Length: About 1 cm. Width: About 3 mm. Shape: Oblong to ovate. Apex: Acute. Base: Truncate. Margin: Entire. Texture, upper and lower surfaces: Densely pubescent. Color, immature, upper surface: Close to 143C; stripes towards the base, close to 47A. Color, immature, lower surface: Close to 143B; stripes towards the base, close to 47A. Color, mature, upper surface: Close to 143C tinted with close to 47A. Color, immature, lower surface: Close to 144A tinted with close to 46A.

*Peduncle* (*umbel stem*).—Length: About 14 cm to 17 cm. Diameter: About 2 mm. Strength: Strong. Angle: Erect to about 30° C. from vertical. Texture: Pubescent. Color: Close to 146B.

*Pedicel* (*individual flower stem*).—Length: About 2.5 cm to 3 cm. Diameter: About 1 mm to 2 mm. Strength: Moderately strong. Angle: Erect to about 60° C. from vertical. Texture: Pubescent. Color: Close to 183A.

*Reproductive organs.*—Androecium: Stamen quantity per flower: About one to ten. Filament length: About 5 mm to 6 mm. Filament color: Close to 161A. Anther length: About 2 mm to 3 mm. Anther shape: Oblong. Anther color: Close to 161A. Pollen amount: Moderate. Pollen color: Close to 33B. Gynoecium: Pistil quantity per flower: One. Pistil length: About 9 mm to 12 mm. Stigma shape: Tapering; reflexed. Stigma color: Close to 45A. Style length: About 4 mm to 5 mm. Style color: Close to 45A. Ovary color: Close to 143A.

*Seed.*—Seed development has not been observed.

Disease/pest resistance: Plants of the new Zonal *Geranium* have not been observed to be resistant to pathogens and pests common to Zonal *Geranium*.

Garden performance: Plants of the new Zonal *Geranium* have been observed to tolerate rain, wind, and temperatures ranging from about 0° C. to about 40° C. and have demonstrated good garden performance.

It is claimed:

1. A new and distinct Zonal *Geranium* plant named 'Fisum Dark Red' as illustrated and described.

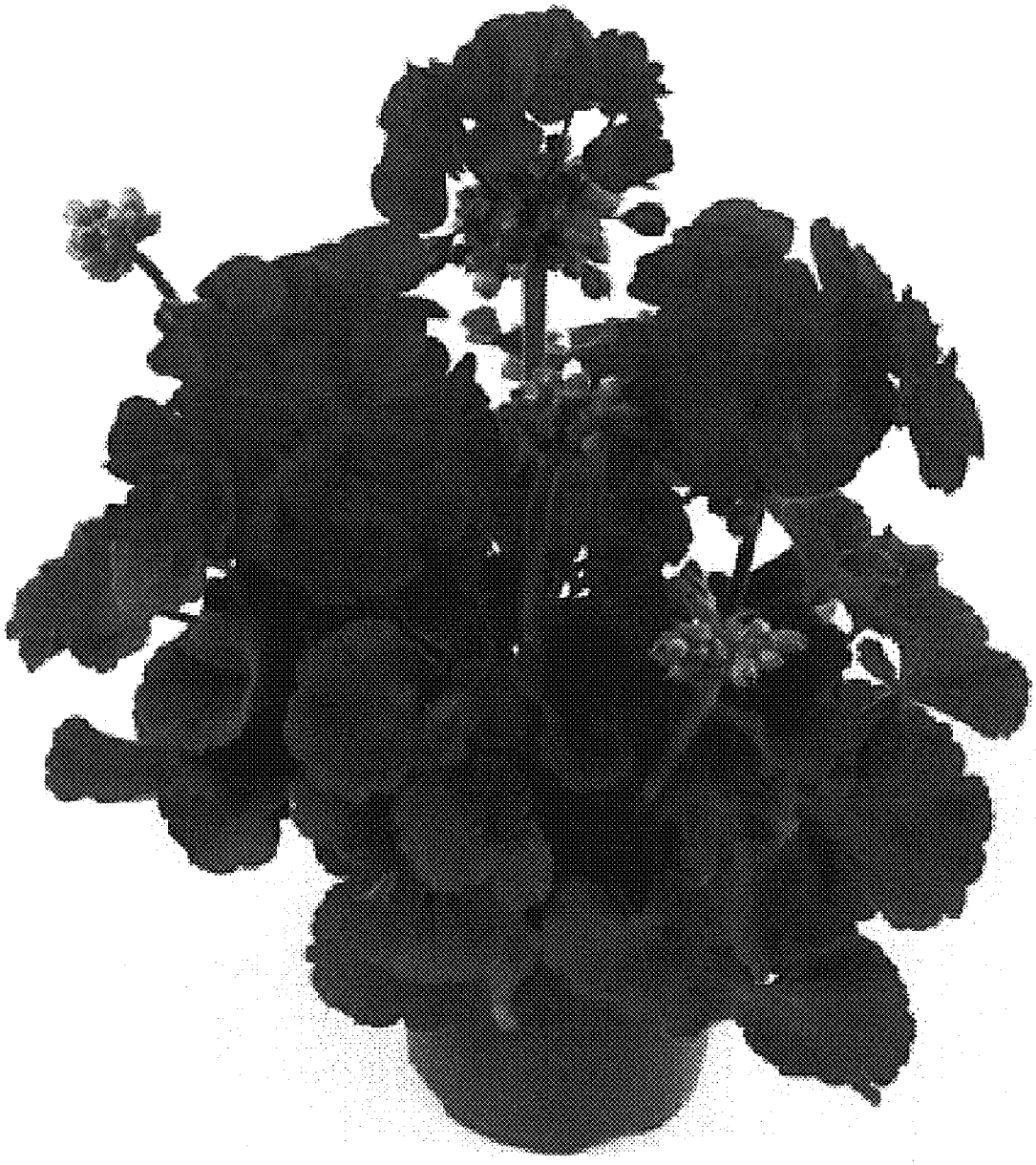

* * * * *